US006454759B2

(12) United States Patent
Krulevitch et al.

(10) Patent No.: US 6,454,759 B2
(45) Date of Patent: Sep. 24, 2002

(54) MICROFABRICATED INJECTABLE DRUG DELIVERY SYSTEM

(75) Inventors: Peter A. Krulevitch, Pleasanton; Amy W. Wang, Oakland, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/795,384

(22) Filed: Feb. 28, 2001

Related U.S. Application Data

(60) Provisional application No. 60/185,527, filed on Feb. 28, 2000.

(51) Int. Cl.[7] .............................. A61K 9/22; A61F 2/00
(52) U.S. Cl. ............................. 604/891.1; 604/892.2; 424/423
(58) Field of Search ........................ 604/890.1, 891.1, 604/892.1, 30, 61, 131, 150, 288.01; 424/422, 423, 424, 400

(56) References Cited

U.S. PATENT DOCUMENTS

| | | | | | |
|---|---|---|---|---|---|
| 4,326,524 A | * | 4/1982 | Drake, Jr. et al. | ........... | 128/260 |
| 4,425,117 A | * | 1/1984 | Hugemenn et al. | ........... | 604/93 |
| 4,585,652 A | * | 4/1986 | Miller et al. | ................... | 424/83 |
| 4,838,862 A | * | 6/1989 | Baker et al. | ............. | 604/892.1 |
| 4,976,966 A | * | 12/1990 | Theeuwes et al. | .......... | 424/473 |
| 5,151,093 A | | 9/1992 | Theeuwes et al. | ........ | 604/292.1 |
| 5,170,801 A | * | 12/1992 | Casper et al. | ................ | 128/769 |
| 5,217,449 A | * | 6/1993 | Yuda et al. | .............. | 604/890.1 |
| 5,368,571 A | * | 11/1994 | Horres, Jr. | .................. | 604/131 |
| 5,874,214 A | * | 2/1999 | Nova et al. | ..................... | 435/6 |
| 6,059,736 A | * | 5/2000 | Tapper | ....................... | 600/573 |
| 6,142,972 A | * | 11/2000 | Cheikh | ........................ | 604/57 |
| 6,217,906 B1 | * | 4/2001 | Gumucio et al. | ........... | 424/473 |
| 6,349,740 B1 | * | 2/2002 | Cho et al. | .................... | 137/807 |

OTHER PUBLICATIONS

"Pumps/Osmotic", Alza Corporation, pp. 896–906.
P. Krulevitch et al, "Thin Film Shape Memory Alloy Microactuators", IEEE, vol. 5, No. 4, Dec. 1996, pp. 270–282.

* cited by examiner

*Primary Examiner*—Sharon Kennedy
(74) *Attorney, Agent, or Firm*—L. E. Carnahan; Alan H. Thompson

(57) ABSTRACT

A microfabricated, fully integrated drug delivery system capable of secreting controlled dosages of multiple drugs over long periods of time (up to a year). The device includes a long and narrow shaped implant with a sharp leading edge for implantation under the skin of a human in a manner analogous to a sliver. The implant includes: 1) one or more micromachined, integrated, zero power, high and constant pressure generating osmotic engine; 2) low power addressable one-shot shape memory polymer (SMP) valves for switching on the osmotic engine, and for opening drug outlet ports; 3) microfabricated polymer pistons for isolating the pressure source from drug-filled microchannels; 4) multiple drug/multiple dosage capacity, and 5) anisotropically-etched, atomically-sharp silicon leading edge for penetrating the skin during implantation. The device includes an externally mounted controller for controlling on-board electronics which activates the SMP microvalves, etc. of the implant.

18 Claims, 6 Drawing Sheets

MICROFABRICATED INJECTABLE DRUG DELIVERY SYSTEM

RELATED APPLICATION

The application relates to U.S. Provisional Application No. 60/185,527 filed Feb. 28, 2000, and claims priority thereof.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to drug delivery systems, particularly to implantable drug delivery systems, and more particularly to an implantable, microfabricated, fully integrated drug delivery system capable of secreting controlled dosages of multiple or single drugs over long periods of time.

Historically, pharmaceutically active agents have been chosen based on biological activity, with absorption, efficacy, and side effect profiles determined by metabolic process. The effectiveness of the therapeutic agent can be enhanced by sophisticated drug delivery systems that actively control the delivery rate and site of drug action.

Alza Corporation, Palo Alto, Calif., has developed a drug delivery system that uses osmotic pressure to infuse drugs, as exemplified by U.S. Pat. No. 5,151,093 issue Sep. 29, 1992. Also Alza Corporation has developed an implantable drug delivery system using osmotic pressure which basically consists of a titanium tube having a water-permeable membrane on one end, and containing a salt pellet, piston, and drug, with an orifice on the opposite end. Water diffuses through the membrane and creates a high concentration NaCl solution by dissolving the salt pellet. Additional water is driven into the device due to the concentration gradient across the membrane, generating osmotic pressures as great as 3000 psi. The pressure pushes on the piston and forces the drug through the orifice at a constant rate. The implantation is performed using a trocar (large syringe) by a physician, after which drug delivery is automatic, eliminating the rests of patients forgetting to take prescribed medication. For infections diseases such as hepatitis, implants such as these will avoid the creation of drug-resistant strains by patients who neglect to complete their prescribed drug schedule. In addition these systems will aid individuals in long-term health management such as hormone therapy.

The prior implantable systems can be improved considerably by reducing the size and adding flow control to enable variable and programmable dosage profiles. This invention allows for delivery of multiple drugs over a period of time and can be programmed or externally controlled. And can be powered by a number of means: 1.) Osmosis; 2.) Thermopneumatic; 3.) Thermal bimorphs; 4.)Shape memory films; 5.) Piezoelectric bimorphs. The drug delivery system having multiple channels to allow for controlled delivery profiles, precise drug metering, and the ability to independently control delivery of several drugs or drug combinations with the same device. The miniature device of the present invention can be implanted prophylactically and lie dormant until activated in response to a therapeutic need by an externally located controller via implanted electronics. Thus, the present invention enables the administering of any drug (vaccines, booster, hormones, antibiotics, etc.) at either discrete time intervals or at a specified rate, such as to soldiers in a controlled manner or in response to a chemical/biological warfare attack.

SUMMARY OF THE INVENTION

It is an object of the present invention to provide a microfabricated in injectable drug delivery system.

a further object of the invention is to provide an implantable drug delivery system which may be controlled externally.

a further object of the invention is to provide an implantable, osmotic engine-based drug delivery system, which utilizes polymer pistons for isolating the pressure source from drug-filled microchannels.

Another object of the invention is to provide a micromachined implantable, osmotically driven drug delivery system utilizing shape memory polymer valves for controlling the osmotic engine and drug outlet ports.

Another object of the invention is to provide an implantable drug delivery device which includes an anisotropically-etched, atomically-sharp silicon leading edge for penetrating the skin during implantation.

Another object of the invention is to provide a drug delivery device of a stacked modular disc-shaped design incorporating membranes for displacing the drugs.

Another object of the invention is to provide a pumping and valving arrangement that could also be used to deliver samples, reagents, and other fluids in ex-vivo microfluidic-based medical diagnostic instruments.

Other objects and advantages of the present invention will become apparent from the following description and accompanying drawings. Basically the invention involves a microfabricated injectable drug delivery system which includes an inplantable, osmotically driven device controlled by shape memory polymer valves which can be activated by an external controller. The implantable osmotic driven device utilizes microfabricated polymer pistons for isolating the pressure source from drug-filled microchannel (an equivalent to microscale syringes). The implantable device is scalable to accommodate a broad range of desired drugs and/or drug volumes. Potential applications for the invention include response to detection of biological or chemical warfare threats, regulated delivery of vaccines or boosters (e.g. anthrax—9 boosters over 18 mos.), hormone therapy, on—demand pain medication and insulin delivery for diabetes management. A demonstration embodiment of a silicon and glass-based device includes an array of four parallel osmotic pumps fabricated on a single 4 mm×1 mm×25 mm member.

BRIEF DESCRIPTION OF THE DRAWINGS

The accompanying drawings, which are incorporated into and form a part of the disclosure, illustrate embodiments of the invention and fabrication method for the control valves thereof and, together with the description, serve to explain the principles of the invention.

DETAILED DESCRIPTION OF THE INVENTION

The present invention is directed to a microfabricated injectable drug delivery system. The system enables the remotely controlled delivery of therapeutic agents (such as broad-spectrum antibiotics, vaccines or neuroprotective agents) in preparation for, and response to, biological and chemical (BN/CW) threats. The invention is a self-contained biofluidic microsystem with on-board control electronics capable of controlled delivery of therapeutic substantances to an individual. The system includes a miniature device to be implanted prophylactically and lie dormant until activated in response to a therapeutic need. The device can be activated on demand in response to a threat, or it can be programmed to deliver multiple doses according to a pre-determined schedule, such as for vaccine boosters. The system includes an interface to the implanted device, which is a hand-held or externally worn control unit, which also inductively couples electromagnetic power into the implanted device for the on-board electronics. Commands may be delivered to the control unit by radio communication. The system will function over periods ranging from months to years. The fully integrated delivery system will be capable of dispensing controlled dosages of multiple therapeutics.

The heart of the system is an osmotic pressure source that uses energy stored I the form of a concentration potential to generate thousands of psi working pressure. A solute-filled chamber is exposed to a fluid across a semipermeable membrane. Water diffuses through the membrane to balance the concentration of dissolved solute, and in the process raises the pressure within the osmotic chamber. The pressure will displace a polymeric micro-piston, which will eject a stored therapeutic agent. Multiple osmotic micropumps can be microfabricated in an array to form what is called an "osmotic engine". Fluid control of each individual chamber in the array will be achieved with temperature controlled shape memory polymer valves activated by remote electronics. The osmotic engine chambers can be loaded with different agents for delivery of multiple therapeutics. Alternatively the chambers can be loaded with discrete does of a single therapeutic. Time of release and rate of agent delivery is pre-programmable in either application.

The drug delivery system of the present invention includes: 1) on-chip self-powered osmotic engine/fluidic manifolds; 2) integrated polymeric micropistons for delivering fluids (drugs); 3) addressable arrays of low power microfabricated shape memory polymer fluid control elements; 4) energy harvesting of extracellular fluid to drive osmotic pressure generation; and 5) RF-powered electronics for remote control and programming. The invention involves the combining of micro pumps, shape memory polymer valves, polymeric micropistons for delivering fluids, on-chip or on-board electronics, and an externally located controller/activator.

Figure 1:
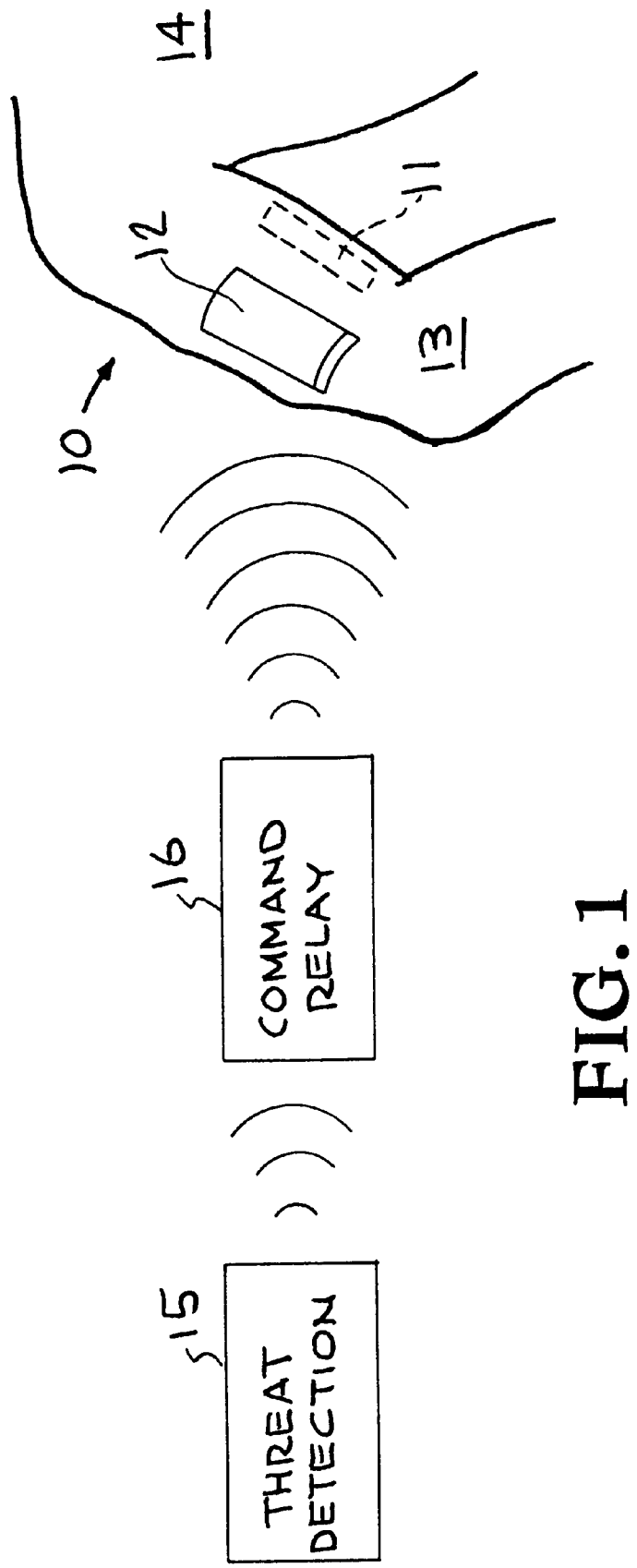
FIG. 1 illustrates an overall view with an enlarged section of an implanted drug pump activated by a threat detection.

Referring now to the drawings, FIG. 1 illustrates an application of the present invention wherein a human being wearing an implanted drug pump and an external controller is provided with drugs in response to a threat detection via a command relay. As shown a drug delivery system 10 which includes an implanted pump 11 and an external controller 12 on an arm 13 of a human body 14 is activated by a threat detection 15 via a command relay 16, whereby the body is protected from exposure to biological/chemical materials by injection of an appropriate anti-material drug via the implanted pump.

Figure 2:
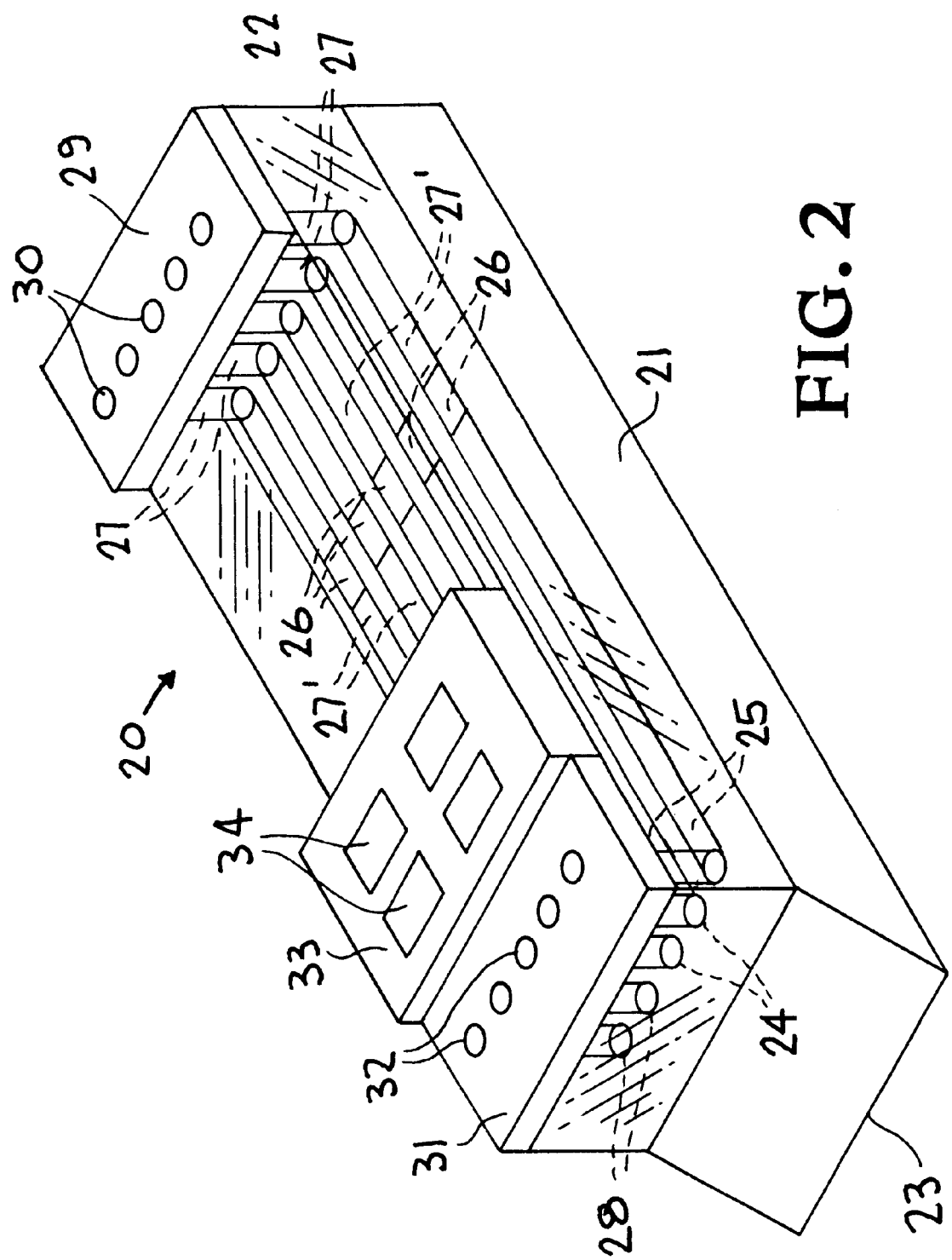
FIG. 2, illustrates an embodiment of a microfabricated, implantable, multi-channel drug delivery device made in accordance with the present invention.

FIG. 2 illustrates an embodiment of an implanted pump 11 of FIG. 1 for the microfabricated drug delivery system of this invention. As shown, a glass substrate or member with drilled or etched holes is bonded to a silicon wafer or substrate with etched microchannels. The silicon has an anisotropically etched sharp leading edge for penetrating the skin of a user. This eliminates the need for an incision or a trocar for implanting the device. The silicon and glass members are bonded together, forming a hermetic seal. It is possible to seal the electronics within the two substrates to protect them from the body. The device of FIG. 2 also could be made from polymeric or other materials. Shape memory polymer (SMP) valve arrays control fluid flow into and out of the device. The polymer may be micromolded such that it contains small holes or pores that open upon heating. Alternatively the valve may rely on control of the inherent material porosity by heating or cooling for controlling fluid flow. Silicon or glass substrates with etched features serve as the mold for the polymeric valves. One possible method for heating the valves locally is to use embedded resistive heater arrays. Once open, the SMP valves remain open, and thus are called "one-shot" valves. Pre-programmed or telemetry-equipped electronics control the operation of the valves. The outlet valves could also be pressure activated such as a polymer membrane with a slit that isolates the drug from the body until pressure from the osmotic engine forces the drug to leak out of the microchannel. The polymer pistons are designed so as not to leak any fluid there passed in either direction.

The microchannels within the implant or device contain pistons or plugs that isolate the drug reservoir from the NaCl (or other osmotic salt). These plugs are injected or inserted into the channel and may be made from polymers, rubbers, foams, or other materials. To form a seal within the microchannels, expanding polymers or polymers that swell when exposed to fluids may be used. Selectively opening the inlet valves allows extra cellular body fluid to permeate the NaCl, thus creating an osmotically induced pressure across the valve membrane. When the outlet valve to the same microchannel is opened, the pressure drives the piston, and the drug is delivered into the body at a rate determined by the induced pressure and the pore or orifice size of the outlet valve. Other valves can be sequentially opened at designated times to produce the desired drug delivery profile.

Figure 3:
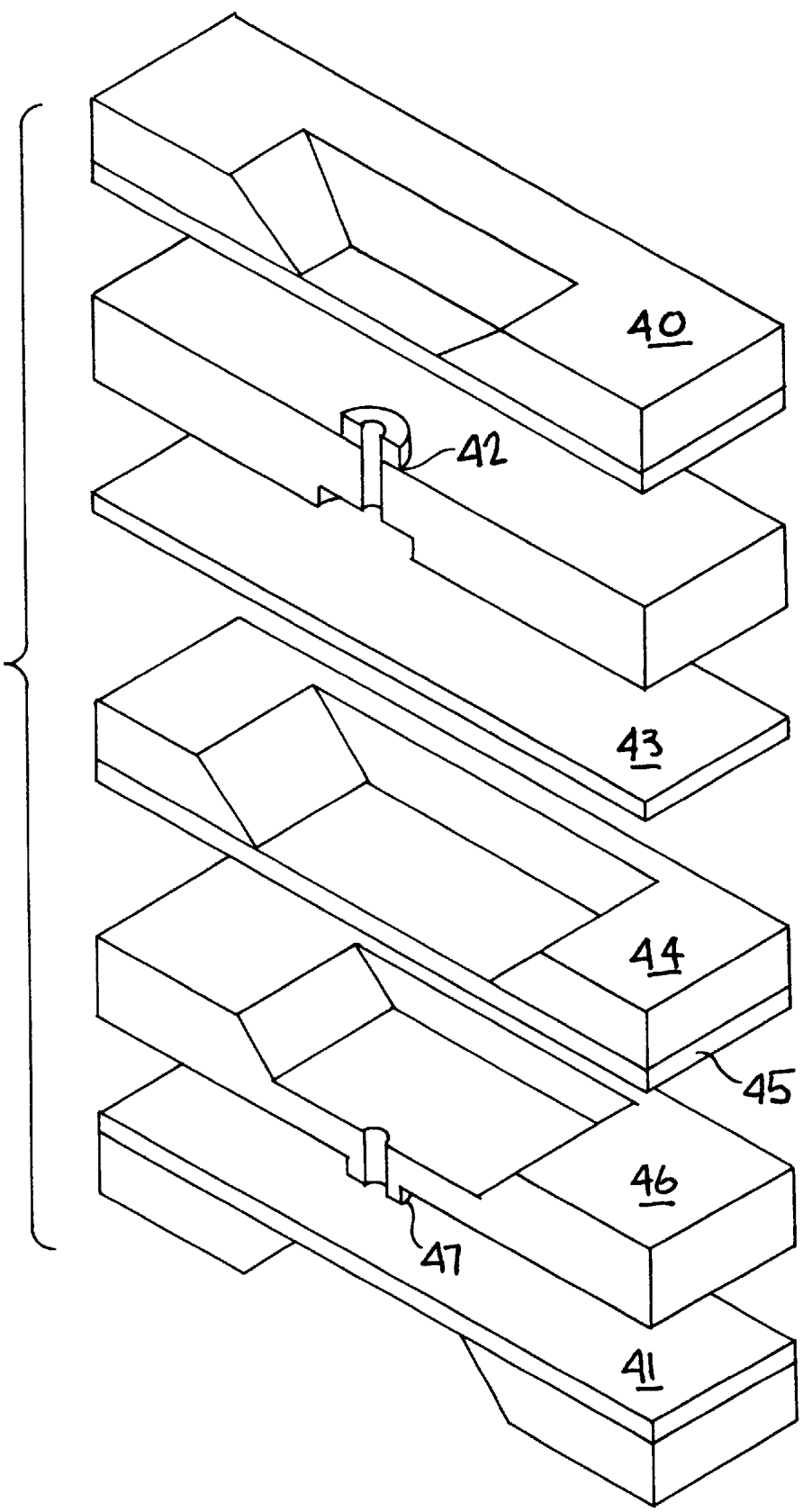
FIG. 3 illustrates an embodiment of a stacked modular disc-shaped design incorporating membranes for displacing the drugs.

As seen in FIG. 2, the implant or device, generally indicated at 20 comprises a silicon substrate or member 21 and a glass substrate or member 22 bonded together, with the silicon substrate 21 have a sharp lead edge 23 for device insertion (penetration under the skin). The silicon substrate 21 is provided with a plurality of microchannels 24, five in this embodiment but with only four being drug filled as indicated at 25. Microchannels 24 also contain a plurality of polymer plugs or pistons 26 and contain a quantity of NaCl, with the polymer pistons design to prevent leakage between the NaCl filled section and the drug-filled section of microchannels 24. The glass substrate 22 is provided with an array of inlet openings 27 and an array of outlet openings 28, each opening array be located at and in communication with ends of microchannels 24. Mounted on the glass substrate 22 is a layer of polymer material 29 having an array of shape memory polymer (SMP) inlet valves indicated at 30 therein which align with inlet openings 27; and a layer of polymer material 31 having an array of shape memory polymer (SMP) outlet valves indicated at 32 which align with outlet opening 28. Also mounted on glass substrate 22 is a layer 33 of material, composed of a silicon cup on which is mounted telemetry and control circuitry indicated at 34 (see FIG. 7B). The NaCl 27' in microchannels 24 could be replaced with material such as KCL, or any salt material suitable for generating sufficient osmotic pressure. FIG. 3 shows an alternative design for the implantable device of FIG. 2, and uses a stacked modular approach with two microfabricated valves, a water permeable membrane, an NaCl reservoir, a super elastic NiTi membrane, a drug reservoir and an outlet control valve. When the inlet valve is opened, interstitial fluid diffuses across the water permeable membrane and permeates the NaCl, creating the osmotic pressure. This pressure causes the super elastic NiTi membrane to bulge, displacing drug from the drug reservoir through the outlet orifice. The outlet valve regulates flow of the drug into the body, super elastic NiTi films enable exceptionally large displacements, and consequently allow for increased drug volume delivery.

As shown in FIG. 3, the stacked modular embodiment comprises a pair of microfabrication inlet and outlet control valves 40 and 41, an inlet regulator 42, a water permeable membrane 43, an NaCl reservoir 44, a super elastic NiTi membrane 45, a drug reservoir 46, and an outlet regulator 47.

Microfabrication techniques are available to construct the various components or sections of the implant or device of FIG. 2. Bulk etching of silicon and glass is a common technique for micromachining channels. Here, it is critical to have a liquid-tight seal across the piston or plug to ensure accurate dose delivery. Factors that influence sliding and sealing characteristics of the piston include the materials of the piston and the microchannels, channel cross-section, channel roughness, piston length, and applied pressure. Tests have shown that channels can be formed by isotropically etching resulting in microchannels with rounded corners.

The piston or plug is most readily moved through a microchannel having a configuration corresponding to the external configuration of the plug. Generally, a circular shaped microchannel and corresponding configured plug is preferable, although other shapes having rounded corners are acceptable. Recently a process has been developed for producing circular microchannels in glass, and is described and claimed in copending U.S. application Ser. No. 09/851,231, filed May 7, 2001, entitled "Method for Producting Microchannels Having Circular Cross-Sections in Glass", assigned to the same assigned. In that method a substrate having etched microchannels is bonded to a top plate and then annealed to allow surface tension forces and diffusional effects to lower the overall energy of the microchannels by transforming the crosssection to a circular shape. Another approach to the formation of circular cross-section microchannels involves embedding of wires or round members of a desired diameter into a (PDMS) substrate, and then pulling out the wire or member following the curing process which creates perfectly circular channels. This results in a flexible microfluidics device with perfectly circular and smooth channels that can be applied in various biomedical microdevice and other microsystems. This process is both time and cost effective due to its simplicity and quick turn around time. The channels can be fabricated in an hour and the cost is tremendously reduced since no silicon is used. An example of a channel made using this technique has been shown in an SEM cross-sectional image, and small hard balls have been loaded into these soft PDMS channels and have been driven with an external pneumatic actuator (syringe). Fluid was successfully pumped using the microsyringe, with the balls forming effective seals against the PDMS microchannels.

Figure 4A:
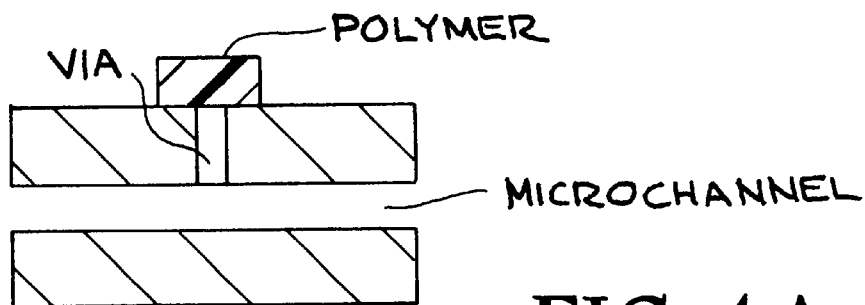
FIGS. 4A–4C illustrate the fabrication of a polymer micropiston for driving the drugs.
Figure 4B:
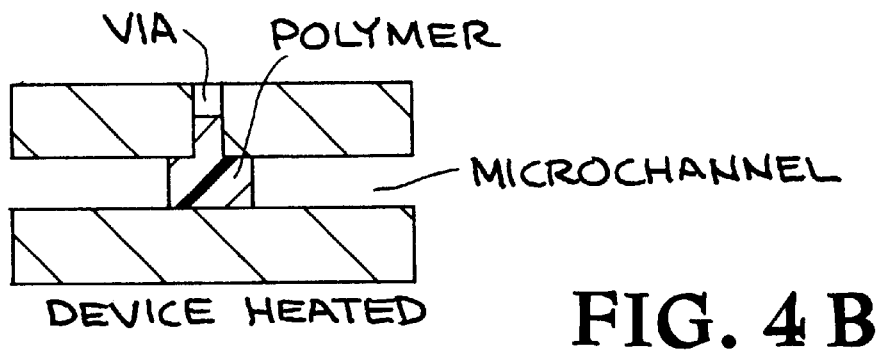
Figure 4C:
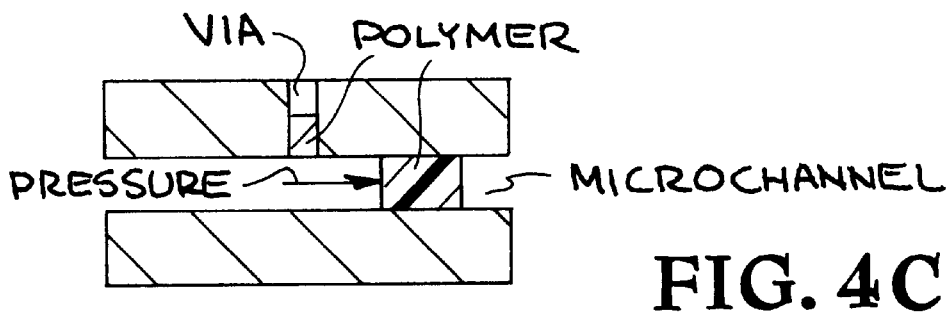

Using the microchannel itself as a precision mold to ensure consistent sealing and sliding characteristics, silicon micropistons have been produced. FIGS. 4A–4C illustrate the micropiston fabrication process. First, a thermoplastic polymer is deposited and patterned on the osmotic engine substrate, as shown in FIG. 4A. Next, heating the substrate causes the polymer to liquefy, and capillary forces pull the polymer into the microchannel, which acts as a precision mold for the micropiston, as shown in FIG. 4B. Finally, when pressure is applied to the microchannel, the micropiston slides within the channel, shearing off a portion that remains to seal the polymer via, as seen in FIG. 4C.

Figure 5:
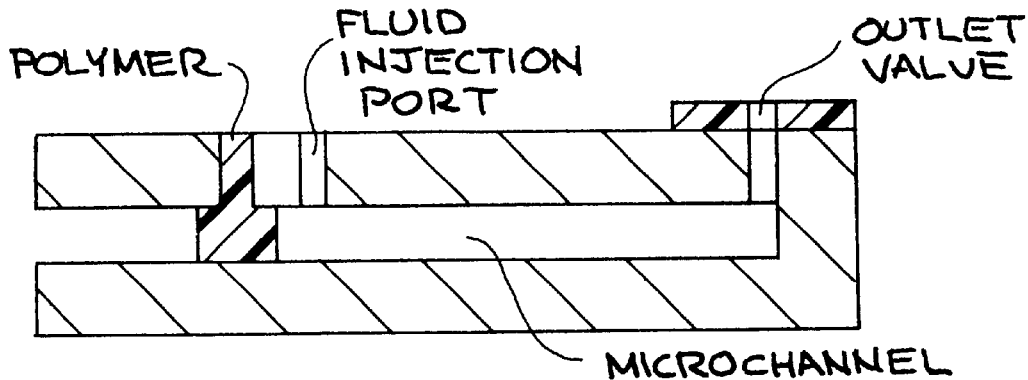
FIG. 5 illustrates the loading of microchannels with fluid after fabricating the osmotic engine.

After fabricating the osmotic engine, the drugs to be delivered by the system are introduced through fluid injection ports, as shown in FIG. 5. After filling, the ports are sealed. Multiple ports can be filled simultaneously with various fluids using robotic feeders such as those used to interface with microtiter plates.

Two basic approaches to valve structure have been considered. The first can be considered as passive where SMP simply pinches off access to the micro-osmotic pump actuator. A second approach involves valves that exploit control of SMP porosity.

Figure 6A:
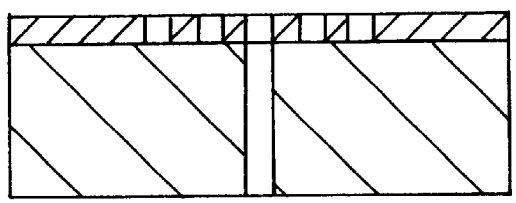
FIG. 6A–6G illustrates a shape memory polymer valve fabrication process sequence.
Figure 6E:
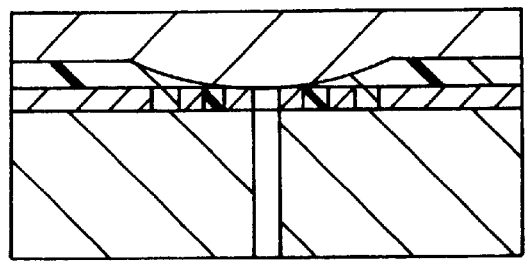
Figure 6B:
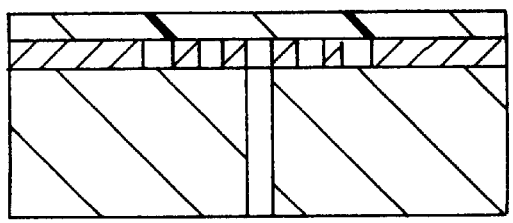
Figure 6F:
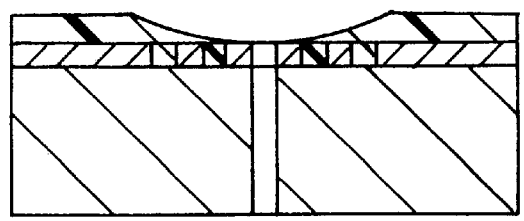
Figure 6C:
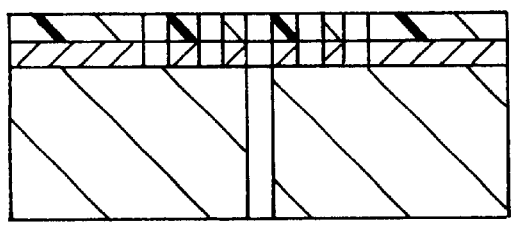
Figure 6G:
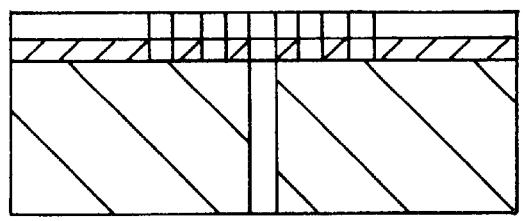
Figure 6D:
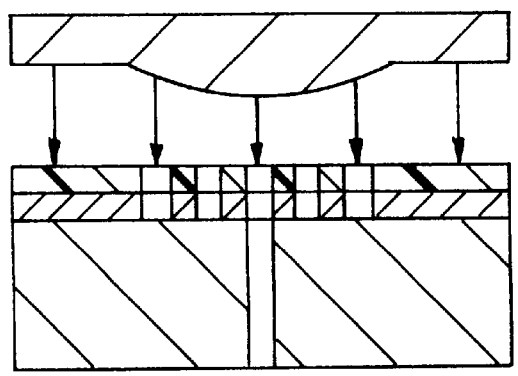

In the first approach, the valves will be closed in the deformed, hard state of the SMP material. Remotely addressable on-board electronics will heat selected valves, causing them to return to the remembered, open state. In the second approach, the osmotic engine will be regulated using individually addressable controlled permeability shape memory polymer microvalves. When sealed, the osmotic solute inside the device will be isolated from the extra cellular fluid. Heating selected polymer patches using addressable embedded resistive heaters will cause pores within the SMP to open, allowing water to diffuse through the polymer and hydrating the osmotic solute. The shape memory polymer controlled-permeability valves may be fabricated as illustrated in FIGS. 6A–6G. The batch process will enable multiple microvalves to be fabricated and sealed simultaneously on the same substrate. The SMP valve fabrication process sequence is as follows:

1. pattern resistive heater over inlet port, see FIG. 6A;
2. deposit shape memory polymer, see FIG. 6B;
3. pattern pores into SMP, see FIG. 6C;
4. heat SMP and mate with mold, see FIG. 6D;
5. mold SMP, see FIG. 6E;
6. remove mold—pores are sealed, see FIG. 6F; and
7. heat SMP to open pores, see FIG. 6G.

The osmotic pump chamber has two valves or two arrays of valves. The input valve or valve array will permit extra cellular fluid to enter a specific (or all) osmotic pump channel. The output valve or valve array will activate release of the drug in the associated reservoir or reservoirs. Multiple reservoirs can be actuated independently, or simultaneously, such that a liquid or drug can be delivered at specific times, or multiple types of drugs can be delivered.

Addressable integrated heaters will be used to actuate the valves. The heat necessary to surpass the SMP glass transition temperature can be supplied in a variety of ways. For example, integrated thermal elements consisting of serpentine coils of conducting thin films can be used. Possible films include platinum and polysilicon and will be in contact with the SMP to provide efficient thermal transfer. The shape memory polymers can also be embedded with conducting particles to improve uniform heating. Thin film conductors can be deposited, as in FIG. 6B, prior to the SMP materials. Subsequent molding deposition of SMP will yield a suspended thin film layer above the SMP layer.

Figure 7A:
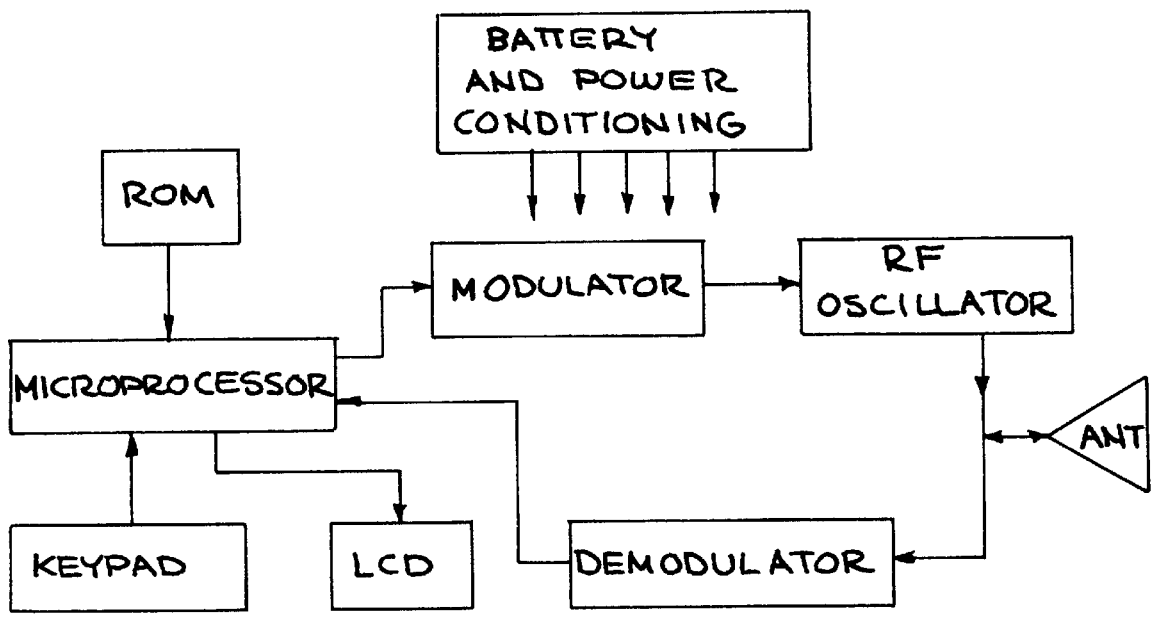
FIGS. 7A–7B set forth a block diagram of controller and on-board electronics for the device of FIG. 2.

FIG. 7A shows the block diagram of the control unit. It is activated by means of a keypress on the keypad. The user will be able to either activate one or more valves or query the on-board electronics as to which valves have been already been activated. The controller will be constructed in a plastic enclosure small enough to be handheld. The circuits will be of hybrid construction using surface mount components. If necessary, an ASIC will be fabricated in the second and third generation versions. A stored program in the ROM controls the operation of the microprocessor. The microprofessor either sends the appropriate valve opening code or status query code to the Modulator or receives response form the Demodulator to a prior status query. The status query response form the on-board electronics will be in the form of coded time-varying power demands imposed on the controller by the on-board electronics. These demands will result in the voltage amplitude at the antenna varying as a function of time. The demodulator will convert the coded time variations to baseband where they can be interpreted by the microprocessor.

The transmission of signals and power over the RF link will be in the 1–10 MHz range so that the size of the antennas and other components can be minimized. During the entire time the control unit is activated, a large amplitude carrier signal will be continuously sent to the on-board electronics to provide the needed power. Information and commands will be encoded as amplitude modulation on the carrier.

The signal from the on-board antenna will be full-wave rectified, filtered, and regulated by a voltage regulator to provide the needed dc voltages for the rest of the on-board electronics. During the short time intervals when the carrier amplitude is low because of signal modulation or when the on-board unit is sending status information to the controller, power will be supplied from stored energy in the rectifier filter capacitor. The amount of energy drain during these short time intervals will only be a small fraction of the stored energy.

Figure 7B:
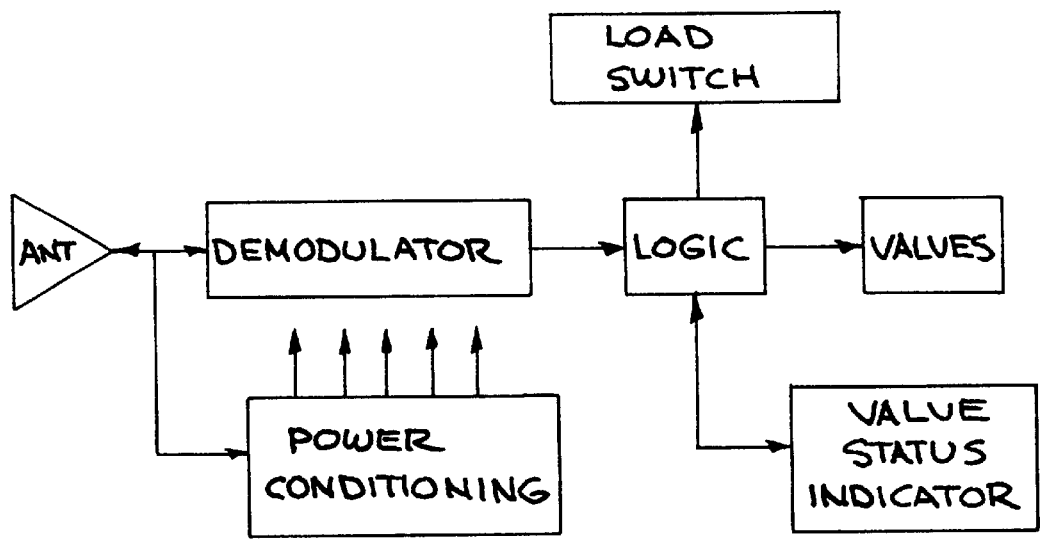

The block diagram of the on-board pump array electronics is shown in FIG. 7B. When the on-board antenna receives a signal from the controller, the power conditioning circuit establishes the voltages needed to power the rest of the on-board electronics. The unit begins operation in a default state of receiving information from the controller. After a handshaking protocol is completed, the unit is ready to receive commands. As information is received, the signal is demodulated, decoded by the logic and the logic then issues appropriate commands to either open valves or query their status. If a status query is issued, the response is encoded by the logic and sent to the load switch. The load switch which activates a dummy load in a coded time-varying manner in order to vary the power demanded by the chip from the control unit.

Indication of valve status will be accomplished by a passive indictor read by the logic, which does not require any electrical power when the control unit is off. Several possibilities exist for the status indictor including a fusible link that is burnt open when the valve is activated or a EPROM like memory cell that stores a logic "1" when the valve is activated.

The antennas for the electronics will be multi-turn pancake coils with a diameter of approximately 1-cm for the coil connected to the controller and approximately 3 mm for the coil on the pump array substrate. Preliminary calculations indicate that ten turns for the controller coil and 50–100 turns for the on-board coil will generate 5–10 volts dc o the pump array wafer at a power level of approximately 10 milliwatts. The first generation coils will be handwound. We will investigate fabricating the second and third generation coils using photolithography and electroplating.

It has thus been shown that the present invention provides a microfabricated, fully integrated drug delivery system capable of secreting controlled dosages of multiple drugs over long periods of time. The implantable drug delivery system of this invention enables administering vaccines, boosters, hormones, or antibiotics in a controlled manner, and is particularly useful in response to a chemical/biological warfare attack. The invention enables controlled drug delivery to patients who might forget to take their medication. As an example, the device would add great convenience to hepatitis and HIV infected patients or individuals ho require hormone therapy who must periodically take drugs over a long period of time.

While particular embodiments, materials, parameters, etc. have been described or illustrated to exemplify and teach the principles of the invention, such are not intended to be limiting. Modifications and changes may become apparent to those skilled in the art, and it is intended that the invention be limited only by the scope of the appended claims.

The invention claimed is:

1. A system for injectable drug delivery, comprising:
   an implantable device having at least one microchannel and containing in at least one drug to be delivered by osmotic pressure,
   valves in said device for at least controlling generation of said osmotic pressure,
   an externally located controller for activating said valves, and
   a piston located in said at least one microchannel intermediate said osmotic device and said at least one drug to be delivered.

2. The system of claim 1, wherein said implantable device comprises a housing having said at least one microchannel in said housing, said at least one drug to be delivered being located in a section of said at least one microchannel.

3. The system of claim 2, wherein said osmotic pressure is generated by an osmotic device located in said it least one microchannel.

4. The system of claim 2, wherein said housing includes a sharp leading edge to assist in implantation thereof.

5. The system of claim 4, wherein said housing is composed of a silicon member and a glass member, said silicon member containing said at least one microchannel in a surface adjacent said glass member.

6. The system of claim 5, wherein said valves are mounted to control opening in said glass member, said openings being in fluid communication with said at least one microchannel.

7. The system of claim 6, additionally including at least electronics for activating said valves, said electronics be constructed to receive activation signals from said externally located controller.

8. The system of claim 7, wherein said electronics are mounted on said glass member.

9. The system of claim 1, wherein said externally located controller is constructed to be activated by detection of a chemical/biological material.

10. The system of claim 1, wherein said valves include shape memory polymer material, and wherein said implantable device includes a heater for said shape memory polymer material for activating said valves.

11. The system of claim 1, wherein said valves include a porous polymeric material, and wherein said implantable device includes a heater for said porous polymeric material for changing the porousity of the polymeric material.

12. The system of claim 2, wherein said housing includes a plurality of microchannels, each microchannel containing a drug and on osmotic device for dispensing the drug from said microchannel when said valves are activated.

13. In an implantable, osmotic driven drug delivery device, the improvement comprising:
   a plurality of microchannels located in said device,
   each microchannel having a drug-filled section,
   each microchannel having an osmotic pressure generating section,
   each microchannel having a piston located intermediate said osmotic pressure generating section and said drug-filled section,
   said piston being constructed to prevent fluid leakage therepast,
   valve means for controlling activation of said osmotic pressure generating section, and valve means for controlling discharge from said drug-filled section.

14. The improvement of claim 13, wherein said valve means comprises shape memory polymer valves.

15. The improvement of claim 14, additionally including means for controlling activation of said shape memory polymer valves.

16. The improvement of claim 15, wherein said microchannels are located in a silicon member, and wherein said silicon member includes a sharp leading edge for assisting in implanting said device.

17. The improvement of claim 16, additionally including a glass member having a plurality of openings are aligned with each of said microchannels.

18. The improvement of claim 17, wherein said valve means comprises a shape memory polymer valve for each of said openings.

* * * * *